US008334357B2

United States Patent
Schieferstein et al.

(10) Patent No.: US 8,334,357 B2
(45) Date of Patent: Dec. 18, 2012

(54) THICKENING AGENT BASED ON POLYURETHANE

(75) Inventors: Ludwig Schieferstein, Ratingen (DE); Oliver Pietsch, Muelheim (DE)

(73) Assignee: Cognis IP Management GmbH, Duesseldorf (DE)

( * ) Notice: Subject to any disclaimer, the term of this patent is extended or adjusted under 35 U.S.C. 154(b) by 912 days.

(21) Appl. No.: 11/630,069

(22) PCT Filed: Jun. 22, 2005

(86) PCT No.: PCT/EP2005/006743
§ 371 (c)(1),
(2), (4) Date: Dec. 10, 2007

(87) PCT Pub. No.: WO2006/002813
PCT Pub. Date: Jan. 12, 2006

(65) Prior Publication Data
US 2008/0108775 A1    May 8, 2008

(30) Foreign Application Priority Data
Jul. 1, 2004    (DE) .......................... 10 2004 031 786

(51) Int. Cl.
*C08G 18/32* (2006.01)
*C08G 18/34* (2006.01)
*C08G 18/28* (2006.01)
*C08L 75/06* (2006.01)
*C08L 75/08* (2006.01)

(52) U.S. Cl. .......... 528/49; 514/844; 524/376; 524/377; 524/591; 528/74.5; 528/76; 528/80; 528/85; 560/26; 560/115; 560/158; 564/44; 564/45

(58) Field of Classification Search ................. 528/74.5, 528/76, 49, 80, 85; 514/844; 524/376, 377; 560/26, 115, 158; 564/44, 45
See application file for complete search history.

(56) References Cited

U.S. PATENT DOCUMENTS
4,079,028 A    3/1978    Emmons et al.
5,500,475 A    3/1996    Eicken et al.
5,756,078 A    5/1998    Oppenländer et al.

FOREIGN PATENT DOCUMENTS
EP    0 787 486 A1    8/1997
WO    WO 93/10166 A1    5/1993

*Primary Examiner* — Rabon Sergent
(74) *Attorney, Agent, or Firm* — Diehl Servilla LLC

(57) ABSTRACT

Disclosed is a thickener based on an aqueous preparation of a nonionic, water-dispersible or water-soluble polyurethane, obtained by reacting: (a) hydrophilic polyols containing at least two OH groups and at least two functional groups selected from ether and ester, of molecular weight at least 300; (b) hydrophobic compounds containing at least one zerewitinoff-active hydrogen atom, of molecular weight about 100 to about 500, with at least one linear or branched, saturated or unsaturated alkyl chain having at least five consecutive carbon atoms not linked to a hetero atom; and (c) at least difunctional isocyanates, where the components are reacted in equivalent ratios $OH_{a)}:ZH_{b)}:NCO_{c)}$ of $1:(1+x):2(1+y)$, with the provisos that x is 0.05-1.2, y is (0.2-1.05)x, and more than one equivalent of $NCO_{c)}$ is present versus the sum of $OH_{a)}$ and $ZH_{b)}$.

16 Claims, No Drawings

THICKENING AGENT BASED ON POLYURETHANE

CROSS REFERENCE TO RELATED APPLICATIONS

This application is the national phase under 35 U.S.C. §371 of PCT International Application No. PCT/EP2005/006743 which has an International filing date of Jun. 22, 2005, which designated the United States of America and which claims priority on German Patent Application No. DE 10 2004 031 786.0, filed Jul. 1, 2004, the entire contents of which are hereby incorporated herein by reference.

FIELD OF THE INVENTION

This invention relates generally to thickeners, and more particularly, to thickeners based on an aqueous preparation of nonionic water-dispersible or water-soluble polyurethanes having a special structure.

BACKGROUND INFORMATION

Polyurethane solutions or dispersions in the form of a water-dilutable aqueous or predominantly aqueous phase are known by the expert as HEUR thickeners (the acronym HEUR derives from "nonionic hydrophobically modified ethylene oxide urethane block copolymer") and have been used for some time now for thickening water-based emulsion paints in various fields of application.

The HEUR thickeners described at the end of the 70s in U.S. Pat. No. 4,079,028 are made up of linear and/or branched polyethylene glycol blocks and hydrophobic segments which are generally linked together by urethane groups (or urea groups where amines are used instead of alcohols).

The thickening effect of HEUR thickeners is assumed to be attributable to the fact that the polyethylene glycol segments ensure compatibility with water while the hydrophobic segments build up a viscosity-generating three-dimensional molecular structure in the emulsion paint to be thickened through an association with one another and with dispersed binder particles of the emulsion paint.

Preferred hydrophobic segments in commercially available HEUR thickeners are relatively long-chain, generally monohydric alcohols, such as for example n-octanol, n-dodecanol, isotridecyl alcohol, isononylphenol or ricinoleic acid methyl ester. These alcohols are predominantly used as such, but also in the form of their addition products with a few equivalents of ethylene oxide.

The polyfunctional isocyanate units predominantly used in commercially available HEUR thickeners are generally difunctional and include, for example, methylene-bis-(4-cyclohexyl)-diisocyanate, m/p-tetramethylene xylylene diisocyanate, hexamethylene diisocyanate, 2,4-toluene diisocyanate, trimethyl hexamethylene diisocyanate or 4/2,4'-diphenylmethane diisocyanate. The polyethylene glycol segments used in commercially available HEUR thickeners are generally also difunctional and have molecular weights of a few thousand dalton, for example 4,500 or 10,000 dalton.

The ratios between the individual constituents of HEUR thickeners, i.e. branched or unbranched polyethylene glycols, mono- or polyfunctional hydrophobic alcohols, pre-ethoxylated mono- or polyfunctional hydrophobic alcohols, chain-extending di- or polyfunctional short-chain alcohols, are generally selected so that one hydrophobic alcohol is available to each ethylene glycol segment end still reactive through a hydroxyl group.

The hydroxyl-terminated synthesis units of HEUR thickeners are joined together by reaction with di- or polyfunctional isocyanates, the equivalent ratios of the isocyanate groups to be reacted with one another in an addition reaction and the "H-acidic" groups (generally OH groups, although they may also be $NH_2$ groups) being selected so that, for every "H-acidic" group equivalent, i.e. generally every OH group, there is at least slightly less than one isocyanate group equivalent. In other words, the equivalent OH:NCO ratio is generally adjusted to a value of at least 1:1, a ratio of 1:1 being ideal or the OH groups outweighing the NCO groups by 5-10% (which corresponds to an equivalent OH:NCO ratio of 1.05:1 to 1.1:1) in order to ensure that the end product (the HEUR thickener) does not contain any free NCO groups which are undesirable on the one hand for toxicological reasons and, on the other hand, because they are capable of entering into unwanted secondary reactions with formulation ingredients when the thickeners are subsequently used in formulations to be thickened. This basic principle, i.e. that, in the production of HEUR thickeners, the OH groups of the polyethylene glycol and hydrophobic alcohol segments slightly outweigh the NCO groups of the isocyanate segments by ca. 5-10%, is also part of the teaching of the above-cited U.S. Pat. No. 4,079,028 (cf. column 3, lines 17 et seq).

HEUR thickeners have recently been acquiring increasing interest as thickeners for disperse cosmetic preparations (cf. for example EP-A 787,486).

SUMMARY OF THE INVENTION

Briefly described, according to an aspect of the invention, a thickener based on an aqueous preparation of a nonionic, water-dispersible or water-soluble polyurethane includes a polyurethane obtainable by the reaction of: (a) one or more hydrophilic polyols which contain per molecule at least two OH groups and at least two functional groups selected from the group consisting of —O— (ether groups) and —COO— (ester groups), the molecular weight of the hydrophilic compounds being at least 300; (b) one or more hydrophobic compounds containing at least one zerewitinoff-active hydrogen atom per molecule, the molecular weight of the hydrophobic compounds ranging from about 100 to about 500 with at least one linear or branched, saturated or unsaturated alkyl chain per molecule, where the alkyl chain has at least five consecutive carbon atoms and is not linked to a hetero atom; and (c) one or more at least difunctional isocyanates, where components (a), (b) and (c) are reacted with one another in equivalent ratios of $OH_{a)}:ZH_{b)}:NCO_{c)}$ of $1:(1+x):2(1+y)$, where $OH_{a)}$ is the primary (terminal) OH groups of component (a), $ZH_{b)}$ is the NCO-reactive functional group containing the zerewitinoff-active hydrogen atom of component (b), and $NCO_{c)}$ is the isocyanate group of component (c), with the provisos that x is a number of 0.05 to 1.2 and y is a number of (0.2 to 1.05)x.

According to another aspect of the invention, a thickener concentrate including water and the thickener described above is also provided.

DETAILED DESCRIPTION OF THE INVENTION

The problem addressed by the present invention was to provide polyurethane-based thickeners which, compared with known polyurethane thickeners, would generate a higher viscosity in the thickened product for the same quantity, despite a lower intrinsic viscosity in their final made-up form. In addition, the thickeners would be able to produced, if desired, without the use of volatile organic solvents.

It has now surprisingly been found that the thickening effectiveness of HEUR thickeners can be distinctly increased if
1. the ratio of (NCO)-reactive functional groups containing at least one zerewitinoff-active hydrogen atom (ZH groups) per molecule of a hydrophobic compound (with alcohols, these would be OH groups) to reactive OH groups of a hydrophilic polyol is increased to well above the usual value of one and
2. distinctly more than one equivalent of polyfunctional isocyanates is made available to the sum of OH and ZH groups.

The present invention relates to thickeners based on an aqueous preparation of nonionic, water-dispersible or water-soluble polyurethanes, these polyurethanes being obtainable by reaction of
(a) one or more hydrophilic polyols (a) which contain per molecule at least two OH groups and at least two functional groups selected from the functions —O— (ether groups) and —COO— (ester groups), the molecular weight of these hydrophilic compounds being at least 300,
(b) one or more hydrophobic compounds containing at least one zerewitinoff-active hydrogen atom per molecule, the molecular weight of these hydrophobic compounds being in the range from 100 to 500 and at least one linear or branched, saturated or unsaturated alkyl chain with at least five consecutive carbon atoms, which is not linked to hetero atoms, being present per molecule of these hydrophobic compounds, and
(c) one or more at least difunctional isocyanates,
characterized in that the compounds a), b) and c) are reacted with one another in equivalent ratios of $OH_{a)}:ZH_{b)}:NCO_{c)}$ of 1:(1+x):2(1+y), with the following provisos:
x is a number of 0.05 to 1.2 and
y is a number of (0.2 to 1.05)x.

The term $OH_{a)}$ denotes the primary (terminal) OH groups of the compounds a). The term $ZH_{b)}$ denotes the NCO-reactive functional groups containing a zerewitinoff-active hydrogen atom b). The term $NCO_{c)}$ denotes the isocyanate groups of the compounds c).

In the context of the present invention, the equivalents of the compounds a) are OH equivalents, the equivalents of the compounds b) are zerewitinoff-active hydrogen equivalents and the equivalents of the compounds c) are NCO equivalents.

Although the notion of the equivalent is familiar to the expert on polyurethane chemistry, its meaning is explained in the following in the interests of clarity.

The term "equivalents" is meant to be interpreted in the usual sense and focuses on the available reactive groups of molecules. For example, 1 mol of a monoalcohol contains 1 mol OH groups; 1 mol of a diol contains 2 mol OH groups, 1 mol of a triol contains 3 mol OH groups and so on. Similarly, 1 mol of a diisocyanate (NCO functionality=2) contains 2 mol NCO groups, 1 mol of a polyisocyanate mixture with a (mean) functionality of 2.3 contains on average 2.3 mol NCO groups and so on. If, for example, alcohols and isocyanates are to be reacted with one another in such a way that the compounds used are to be in certain ratios based on the OH or NCO groups, it is advisable to keep to the ratios of the reactive groups instead of ratios by weight or molar ratios. This OH:NCO ratio is termed the equivalent ratio.

In general terms, the equivalent ratio is the numerical ratio between defined reactive groups in the reactants used.

In the interests of clarity, a practical example of how an equivalent ratio is readily determined is presented in the following:

If, for example,
1 mol of a polyethylene glycol (PEG, OH functionality=2) containing two OH groups per molecule
is reacted in accordance with the teaching of the invention with
4 mol of a hydrophobic alcohol (OH functionality=1) containing one OH group per molecule and
4 mol of a diisocyanate (NCO functionality=2)
to form the polyurethane, then
the PEG used will contain 2 mol OH groups,
the hydrophobic alcohol used will contain 4 mol OH groups and
the diisocyanate used will contain 8 mol OH groups.
The numerical ratio of the OH groups of the polyethylene glycol to the OH groups of the hydrophobic alcohol to the NCO groups of the diisocyanate is thus 2:4:8 or 1:2:4. Or, conversely, if, for example, the components just mentioned (PEG, hydrophobic alcohol and diisocyanate) are to be reacted in an equivalent ratio of 1:3:3, the polyethylene glycol, hydrophobic alcohol and diisocyanate have to be used in a molar ratio of 0.5:3:1.5 or 1:6:3.

In the interests of clarity and unambiguity, it is expressly pointed out that y is obtained by multiplication. Accordingly, the term expressed for y, namely "(0.2 to 1.05)x", means that x—for which a concrete number from the range indicated for x is to be used—has to be multiplied by a number from the range of 0.2 to 1.05.

In one embodiment, the compounds a), b) and c) are reacted with one another in an equivalent ratio of $OH_{a)}:ZH_{b)}:NCO_{c)}$ of 1:(1+x):2 (1+y), where x is a number of 0.05 to 1.2 and y is a number of $(0.2 \text{ to } 1.05)_x$.

In another embodiment, the compounds a), b) and c) are reacted with one another in an equivalent ratio of $OH_{a)}:ZH_{b)}:NCO_{c)}$ of 1:(1+x):2 (1+y), where x is a number of 0.15 to 1.1 and y is a number of (0.5 to 1.03)x.

In a preferred embodiment, the compounds a), b) and c) are reacted with one another in an equivalent ratio of $OH_{a)}:ZH_{b)}:NCO_{c)}$ of 1:(1+x):2 (1+y), where x is a number of 0.3 to 1.05 and y is a number of (0.5 to 1.02)x.

In a particularly preferred embodiment, the compounds a), b) and c) are reacted with one another in an equivalent ratio of $OH_{a)}:ZH_{b)}:NCO_{c)}$ of 1:(1+x):2 (1+y), where x is a number of 0.5 to 1.02 and y is a number of $(0.7 \text{ to } 1.01)_x$.

Components (a)

By definition, the hydrophilic polyols (a) contain per molecule at least two OH groups and at least two functional groups selected from the functions —O— (ether groups) and —COO— (ester groups), the molecular weight of these hydrophilic compounds being at least 300 and preferably at least 1,000. Component (a) is thus the hydrophilic molecular constituent of the polyurethanes according to the invention of the HEUR type. It is expressly pointed out that the compounds (a) differ basically from the compounds (b) which are hydrophilic and not hydrophobic.

Suitable compounds (a) are, for example, the polymerization products of ethylene oxide, copolymerization or graft polymerization products thereof and the polyethers obtained by condensation of polyhydric alcohols or mixtures thereof and by ethoxylation of polyhydric alcohols, amides, polyamides and aminoalcohols. Examples of suitable compounds (a) are polyethylene glycols, products of the addition of ethylene oxide onto trimethylol propane, EO-PO block copolymers, OH-terminated polyesters, such as for example those of the polyfunctional polycaprolactone type.

Preferred compounds (a) are polyether polyols. These are hydrophilic polyols (a) which contain at least two OH groups and at least two —O— functions (ether groups) per molecule.

These polyether polyols are generally so highly hydrophilic that they are soluble in water at room temperature (20° C.).

Polyether polyols at least predominantly containing polyethylene glycol are particularly suitable for the production of the polyurethanes according to the invention. Particularly good results are obtained when these polyethylene glycols have a mean content of alkoxy units of 20 to 400.

Preferred compounds (a) are diols with the general formula HO—($CH_2$—$CH_2$—O)$_n$—H, where n may assume a value of 20 to 400. The compounds are polyethylene glycols which represent condensation products of ethylene oxide with ethylene glycol or water. The molecular weight of these polyethylene glycols is preferably adjusted to a value of 1,000 to 15,000.

Component (b)

Component (b) is a hydrophobic compound containing at least one zerewitinoff-active hydrogen atom per molecule, the molecular weight of this hydrophobic compound being in the range from 100 to 500 and at least one linear or branched, saturated or unsaturated alkyl chain with at least five consecutive carbon atoms, which is not linked to hetero atoms, being present per molecule of the hydrophobic compound. The term "hetero atoms" is known to the expert. Carbon and hydrogen are not, of course, hetero atoms.

It is known that hydrogen attached to N, O or S is termed zerewitinoff-active hydrogen (sometimes even just "active hydrogen") if it yields methane by reaction with methyl magnesium iodide by a process discovered by Zerewitinoff. Typical examples of compounds containing zerewitinoff-active hydrogen are compounds containing carboxyl, hydroxyl, amino, imino or thiol groups as functional groups.

It is crucial to the compounds (b) that the basic skeleton of the molecules of the compounds (b) is largely hydrophobic in character, i.e. has essentially one hydrocarbon radical which may be aliphatic or aromatic-aliphatic. The basic skeleton of the molecules of the compounds (b) is preferably aliphatic, in which case it may be saturated or unsaturated, linear or branched.

Besides the NCO-reactive functional group containing the zerewitinoff-active hydrogen, the compounds (b) may additionally contain one or two other polar groups per molecule. These polar groups may in turn contain functional groups with zerewitinoff-active hydrogen and also such groups as —Cl, —F or Br.

In one embodiment, the hydrophobic alcohols (b), besides their isocyanate-reactive OH group, contain another one or two polar groups that are inert to isocyanates. According to the invention, the additional polar groups are preferably ether, ester, amide and/or oxazoline groups, with the above-mentioned proviso that there are one or two such groups per molecule. Examples include ricinoloxazoline and castor oil fatty acid methyl ester.

The compounds (b) preferably contain 6 to 24 carbon atoms per molecule. These compounds preferably contain only one NCO-reactive functional group containing the zerewitinoff-active hydrogen as the functional group. Examples include alcohols, carboxylic acids and amines containing 6 to 24 carbon atoms per molecule.

Hydrophobic alcohols which must contain one NCO-reactive OH group per molecule are preferably used as the compounds (b). The hydrophobic alcohols preferably contain a total of 6 to 24 carbon atoms per molecule. In addition to the obligatory NCO-reactive OH group per molecule, the hydrophobic alcohols may also contain one or two OH groups. Examples include α,β-diols which are obtainable, for example, by reaction of α-olefins with per acids and subsequent ring opening of the oxiranes obtained with water.

In a particularly preferred embodiment, alcohols containing 6 to 24 carbon atoms and more particularly 8 to 20 carbon atoms per molecule are used as the hydrophobic alcohols (b). These alcohols may be saturated or unsaturated, linear or branched. Fatty alcohols and oxo alcohols with chain lengths in the range mentioned are particularly preferred. Linear saturated alcohols containing 8 to 20 carbon atoms per molecule, which may be used individually or in combination, are most particularly preferred.

The following are examples of suitable alcohols (b):

Strictly linear alcohols from natural sources or from the Ziegler synthesis reaction of ethylene in the presence of aluminium alkyl catalysts. Particularly preferred alcohols (b) of this type are n-octanol, n-decanol, n-dodecanol, n-tetradecanol, n-hexadecanol, n-octadecanol.

More or less heavily methyl-, ethyl-, propyl-, butyl- or higher alkyl-branched alcohols from the oligomerization and co-oligomerization of olefins, for example propylene and/or butylene, optionally together with ethylene, and subsequent noble-metal-catalyzed hydroformylation (other isomerizations optionally taking place). Particularly preferred alcohols (b) of this type are Exxal 8, Exxal 9, Exxal 10, Exxal 11, Exxal 13 from Exxon, i-nonanol from Degussa and i-decyl and i-tridecyl alcohol from BASF.

Alcohols branched in the 2-position. These are the Guerbet alcohols known to the expert which are obtainable by dimerization of primary alcohols through the so-called Guerbet reaction. Particularly preferred alcohols (b) of this type are Isofol 12 from Sasol and Rilanit G16 from Cognis.

Alcohols which are obtained by Friedel-Crafts alkylation with oligomerized olefins and which thus contain an aromatic ring in addition to a saturated hydrocarbon radical. Particularly preferred alcohols (b) of this type are i-octyl phenol and i-nonyl phenol.

Other suitable hydrophobic alcohols (b) are those which contain one or more other polar groups in addition to the obligatory OH group, but only to such an extent that the alcohol as a whole may be classified as a hydrophobic compound. A representative example of such an alcohol is the ricinoleic acid methyl ester marketed by Cognis under the name of "Edenor MeRi".

In one embodiment, the alcohols (b) mentioned may also be used in the form of their alkoxylation products with ethylene and/or propylene oxide.

Components (c)

Suitable isocyanates (c) with a functionality of at least two are any polyfunctional aromatic, alicyclic and aliphatic isocyanates. The suitable polyfunctional isocyanates preferably contain on average 2 to at most 4 NCO groups. Diisocyanates are preferred compounds (c).

Examples of suitable isocyanates are 1,5-naphthylene diisocyanate, 4,4'-diphenylmethane diisocyanate (MDI), hydrogenated MDI ($H_{12}$MDI), xylylene diisocyanate (XDI), tetramethyl xylylene diisocyanate (TMXDI), 4,4'-diphenyldimethylmethane diisocyanate, di- and tetraalkyl diphenyl-methane diisocyanate, 4,4'-dibenzyl diisocyanate, 1,3-phenylene diisocyanate, 1,4-phenylene diisocyanate, the isomers of toluene diisocyanate (TDI), optionally in admixture, 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethyl cyclohexane, chlorinated and brominated diisocyanates, phosphorus-containing diisocyanates, 4,4'-diisocyanatophenyl perfluoroethane, tetramethoxybutane-1,4-diisocyanate, butane-1,4-diisocyanate, hexamethylene diisocyanate (HDI), dicyclohexylmethane diisocyanate, cyclohexane-1,4-diisocyanate, ethylene diisocyanate, phthalic acid-bis-isocyanatoethyl ester, polyisocyanates containing reactive halogen atoms, such as 1-chloromethylphenyl-2,4-diisocyanate, 1-bromomethylphenyl-2,6-diisocyanate, 3,3-bis-chloromethylether-4,4'-diphenyl diisocyanate. Sulfur-containing polyisocyanates are obtained, for example, by reaction of 2 mol hexamethylene diisocyanate with 1 mol thiodiglycol or dihydroxydihexyl sulfide. Other important diisocyanates are trimethyl hexamethylene diisocyanate, 1,4-diisocyanatobutane, 1,2-diisocyanatododecane and dimer fatty acid diisocyanate. Also of interest are partly masked polyisocyanates which enable self-crosslinking polyurethanes to be formed, for example dimeric toluene diisocyanate, or polyisocyanates partly reacted with, for example, phenols, tertiary butanol, phthalimide, caprolactam.

In a preferred embodiment of the invention, the isocyanates (c) used for the production of the polyurethanes at least predominantly contain isophorone diisocyanate (IPDI) and/or tetramethyl xylene diisocyanate (TMXDI). Component (c) is preferably selected solely from the group consisting of isophorone diisocyanate (IPDI) and tetramethylxylene diisocyanate (TMXDI).

In another preferred embodiment, isocyanates with a functionality of 2 (difunctional isocyanates) are used.

In another embodiment, isocyanates with a functionality above 2 are completely or partly used if it desired to produce branched polyurethanes.

Production of the Polyurethanes to be Used in Accordance with the Invention

In principle, the polyurethanes to be used in accordance with the invention may be produced by any of the methods known to the relevant expert. The end products preferably have no free NCO groups or are substantially free from NCO groups. The production process is preferably carried out under water-free conditions, for example by azeotropic removal of water, by heating and passing through a stream of nitrogen or by using water-free reactants. If desired, the production of the polyurethanes may be carried out in a solvent or diluent. This may be necessary in the event of an increase in viscosity during the reaction. The solvent or diluent used should be inert to NCO groups. Suitable solvents/diluents are, for example, benzene, toluene, xylene, cyclohexane, ethyl acetate, butyl acetate and dialkyl ethers of ethylene glycol, diethylene glycol and the like. The solvent/diluent may be in the system from the outset or may be added during and/or after the production of the polyurethanes.

Basically, the reaction temperature is not critical and is preferably in the range from 40 to 130° C. and more particularly in the range from 60 to 115° C. The reaction temperature is preferably selected so that the reaction takes place sufficiently quickly and secondary products are minimized.

In one embodiment, the reaction is carried out in the presence of a catalyst. The catalyst is generally selected from a) metal-containing compounds such as, for example, dibutyl tin diacetate, dibutyl tin dilaurate, dibutyl tin di-(2-ethylhexanoate), tin octoate, tin chloride, potassium oleate, tetra-(2-ethylhexyl)-titanate, cobalt-2-ethylhexanoate, iron-2-ethyl hexanoate, zinc naphthenates, iron chloride and/or b) compounds containing amino groups such as, for example, triethylamine, 1,4-diazabicyclo-octane, 1,8-diazabicyclo-[5.4.0]-undecene.

In principle, the OH:ZH:NCO ratio of the polyurethanes to be used in accordance with the invention, which must contain the constituents (a), (b) and (c), may be varied over a wide range, but with the provisos explained above.

In general, the order in which the compounds (a), (b) and (c) are reacted with one another is determined by the methods generally known to the expert. In one embodiment, the polyether polyol (a) and the isocyanate (c) are first reacted with one another. The intermediate product formed contains allophanate as a result of the equivalent ratios to be maintained as described. The alcohol (b) is then added. In another embodiment, the compounds (a), (b) and (c) are used simultaneously. In this case, it may be desirable to adjust a relatively high reaction temperature within the preferred range mentioned and/or to use a catalyst which promotes the formation of intermediate allophanate structures. In all cases, it is preferred to continue the reaction to the point where the product has only a minimal residual NCO content. This residual NCO content is preferably adjusted to a value of zero, i.e. the course of the reaction is followed by sampling and determination of the NCO content and the reaction is terminated when a residual NCO content can no longer be determined.

Thickener Concentrates

The present invention also relates to thickener concentrates containing (A) water, (B) nonionic, water-dispersible or water-soluble polyurethanes obtainable by reaction of (a) one or more hydrophilic polyols (a) which contain per molecule at least two OH groups and at least two functional groups selected from the functions —O— (ether groups) and —COO— (ester groups), the molecular weight of these hydrophilic compounds being at least 300, (b) one or more hydrophobic compounds containing at least one zerewitinoff-active hydrogen atom per molecule, the molecular weight of these hydrophobic compounds being in the range from 100 to 500 and at least one linear or branched, saturated or unsaturated alkyl chain with at least five consecutive carbon atoms, which is not linked to hetero atoms, being present per molecule of these hydrophobic compounds, and (c) one or more at least difunctional isocyanates, the compounds (a), (b) and (c) being reacted with one another in equivalent ratios of $OH_{a)}:ZH_{b)}:NCO_{c)}$ of $1:(1+x):2(1+y)$, with the following provisos:

x is a number of 0.05 to 1.2 and y is a number of (0.2 to 1.05)x and (C) optionally one or more organic solvents and/or nonionic surfactants in the form of addition compounds of ethylene and/or propylene oxide onto $C_{8-18}$ alcohols.

The foregoing observations apply to preferred embodiments in respect of the compounds (B).

The solvents (C) are volatile organic solvents. Examples of such solvents are low molecular weight alcohols, such as methanol, ethanol, n-propanol, i-propanol, n-butanol, i-butanol, sec.butanol, ethanediol, butanediol, glycerol, trimethylol propane.

Preferred nonionic surfactants in the form of addition compounds of ethylene and/or propylene oxide onto $C_{8-18}$ alcohols (C) are those containing 2 to 4 mol ethylene oxide per mol alcohol. The carbon chain of the alcohols may be saturated or unsaturated, linear or branched. One example of a suitable compound (C) of this class is Dehydrol O4 (a product of Cognis Deutschland GmbH & Co. KG) which is an addition product of 4 mol ethylene oxide per mol octanol.

The present invention relates to the use of the thickeners or thickener concentrates according to the invention for thickening aqueous systems, preferably aqueous dispersions, selected from the group consisting of water-based automotive and industrial paints, printing and textile inks, pigment printing pastes, water-based pharmaceutical formulations, cosmetic formulations or pharmaceutical/cosmetic formulations, plant protection formulations, filler and pigment dispersions, cleaning and coating compositions, preparations of detergents, adhesives, waxes and polishes and for petroleum production.

EXAMPLES

Abbreviations Used

| PEG: | Polyglycol E 8000 (polyethylene glycol from Dow Chemical; hydroxyl value = 13) |
|---|---|
| IPDI: | isophorone diisocyanate (IPDI, Degussa/Hüls) |
| TMXDI: | m-tetramethyl xylene diisocyanate (TMXDI, Cytec) |
| i-$C_{10}$—OH: | isodecyl alcohol (oxomethylated propene trimer; "Exxal 10", a product of Exxon Mobil Chemical) |
| BuOc—OH: | 2-butyl-1-octanol |
| Dehydol O4: | addition product of 4 mol ethylene oxide onto 1 mol n-octanol (Cognis) |

Polyurethane Production

Example 1

For Comparison 207.1 g (24 mmol) Polyglycol E 8000 (polyethylene glycol from Dow Chemical; OHV=13) were introduced into a 1-liter four-necked flask. The flask was then evacuated and purged with nitrogen twice. Vacuum was then applied and the mixture was heated to 100° C. Water was then removed over a period of 2 hours at that temperature under a vacuum of at least 10 mbar. The flask was then purged with nitrogen and the inert gas atmosphere was then maintained by a gentle stream of nitrogen. The contents of the flask were then stirred at 120 r.p.m. for the remainder of the reaction. 7.6 g (48 mmol) isodecyl alcohol and 10.7 g (48 mmol) isophorone diisocyanate (IPDI, Degussa/Hüls) were then added in that order. The reaction temperature was kept at 110° C. during the addition and for the remainder of the reaction. After a reaction time of 1 hour, 0.05 g 1,8-diazabicyclo-[5.4.0]-undec-7-ene (Nitroil) was added as catalyst. When no more residual isocyanate could be detected (which was the case after a total reaction time of ca. 2 hours), 143.6 g Dehydrol O4 deo (addition product of 4 mol ethylene oxide onto 1 mol n-octanol; a Cognis product) was added without further heating or cooling and the whole was stirred to homogeneity. The temperature fell to below 100° C. 359.0 g deionized water were then added with stirring, followed by stirring to homogeneity. Ca. 700 g of a viscous, clear, slightly yellowish polymer solution were isolated from the reaction vessel. The dry residue (which was determined by placing ca. 1-2 g of the polymer solution prepared as described above in a 10 cm aluminium dish and drying for 1.5 h at 105° C. in a recirculating air drying cabinet) amounted to 48.6% by weight and the Brookfield viscosity to 2.75 Pas (Brookfield RVT viscosimeter, spindle 6, 20 r.p.m., 22° C.).

Example 1a

Invention

The procedure was as in Example 1, except that 11.4 g (72 mmol) isodecyl alcohol were used instead of the 7.6 g (48 mmol) used in Example 1 and 15.1 g (68 mmol) isophorone diisocyanate were used instead of the 10.7 g (48 mmol) used in Example 1. In addition, 146.9 g Dehydrol O4 deo were used instead of 143.6 g and 367.3 g deionized water were used instead of 359.0 g. Ca. 730 g of a viscous, clear, slightly yellowish polymer solution were isolated from the reaction vessel. The dry residue amounted to 48.4% by weight. The viscosity of the polymer solution obtained measured 4.75 Pas.

Example 1b

Invention

The procedure was as in Example 1, except that 13.3 g (84 mmol) isodecyl alcohol were used instead of the 7.6 g (48 mmol) used in Example 1 and 16.5 g (74 mmol) isophorone diisocyanate were used instead of the 10.7 g (48 mmol) used in Example 1. In addition, 149.5 g Dehydrol O4 deo were used instead of 143.6 g and 373.8 g deionized water were used instead of 359.0 g. Residual isocyanate could no longer be detected after a reaction time of three hours. Ca. 740 g of a viscous, clear, slightly yellowish polymer solution were isolated from the reaction vessel. The dry residue amounted to 49.1% by weight. The viscosity of the polymer solution obtained measured 4.0 Pas.

Example 1c

Invention

The procedure was as in Example 1, except that 15.2 g (96 mmol) isodecyl alcohol were used instead of the 7.6 g (48 mmol) used in Example 1 and 18.1 g (82 mmol) isophorone diisocyanate were used instead of the 10.7 g (48 mmol) used in Example 1. In addition, 150.8 g Dehydrol O4 deo were used instead of 143.6 g and 377.0 g deionized water were used instead of 359.0 g. Ca. 750 g of a viscous, clear, slightly yellowish polymer solution were isolated from the reaction vessel. The dry residue amounted to 49.2% by weight. The viscosity of the polymer solution obtained measured 5 Pas.

Example 2

For Comparison 207.1 g (24 mmol) Polyglycol E 8000 (polyethylene glycol from Dow Chemical; OHV=13) were introduced into a 1-liter four-necked flask. The flask was then evacuated and purged with nitrogen twice. Vacuum was then applied and the mixture was heated to 100° C. Water was then removed over a period of 2 hours at that temperature under a vacuum of at least 10 mbar. The flask was then purged with nitrogen and the inert gas atmosphere was then maintained by a gentle stream of nitrogen. The contents of the flask were then stirred at 120 r.p.m. for the remainder of the reaction. 8.9 g (48 mmol) 2-butyl-1-octanol, 11.7 g (48 mmol) m-tetramethyl xylene diisocyanate (TMXDI, a Cytec product) and (as catalyst) 0.05 g 1,8-diazabicyclo-[5.4.0]-undec-7-ene (Nitroil) were then added in that order. The reaction temperature was kept at 110° C. during the addition and for the remainder of the reaction. When no more residual isocyanate could be detected (which was the case after ca. 6 hours), 139.1 g Dehydrol O4 deo (addition product of 4 mol ethylene oxide onto 1 mol n-octanol; a Cognis product) were added without further heating or cooling and the whole was stirred to homogeneity. The temperature fell to below 100° C. 347.8 g deionized water were then added with stirring, followed by stirring to homogeneity. Ca. 700 g of a viscous, clear, slightly yellowish polymer solution were isolated from the reaction vessel. The dry residue (which was determined by placing ca. 1-2 g of the polymer solution prepared as described above in a 10 cm aluminium dish and drying for 1.5 h at 105° C. in a recirculating air drying cabinet) amounted to 48.0% by weight and the Brookfield viscosity to 3.25 Pas (Brookfield RVT viscosimeter, spindle 6, 20 r.p.m., 22° C.).

Example 2a

Invention

The following quantities were processed in the same way as in Example 2.
186.3 g (22 mmol) Polyglycol E 8000 (polyethylene glycol from Dow Chemical; OHV=13)
9.9 g (53 mmol) 2-butyl-1-octanol
12.9 g (53 mmol) m-tetramethyl xylene diisocyanate
0.05 g 1,8-diazabicyclo-[5.4.0]-undec-7-ene (Nitroil)
127.1 g Dehydrol 04 deo
317.7 g deionized water.

Ca. 640 g of a viscous, clear, slightly yellowish polymer solution were isolated from the reaction vessel. The dry residue amounted to 48.6% by weight. The viscosity of the polymer solution obtained measured 3.25 Pas.

Example 2b

Invention

The following quantities were processed in the same way as in Example 2.
165.7 g (19 mmol) Polyglycol E 8000 (polyethylene glycol from Dow Chemical; OHV=13)
10.8 g (58 mmol) 2-butyl-1-octanol
12.9 g (53 mmol) m-tetramethyl xylene diisocyanate
0.05 g 1,8-diazabicyclo-[5.4.0]-undec-7-ene (Nitroil)
114.1 g Dehydrol 04 deo
285.2 g deionized water.

Ca. 570 g of a viscous, clear, slightly yellowish polymer solution were isolated from the reaction vessel. The dry residue amounted to 48.9% by weight. The viscosity of the polymer solution obtained measured 3.0 Pas.

Example 2c

Invention

The following quantities were processed in the same way as in Example 2.
207.1 g (24 mmol) Polyglycol E 8000 (polyethylene glycol from Dow Chemical; OHV=13)
13.6 g (73 mmol) 2-butyl-1-octanol
17.2 g (71 mmol) m-tetramethyl xylene diisocyanate
0.05 g 1,8-diazabicyclo-[5.4.0]-undec-7-ene (Nitroil)
143.7 g Dehydrol 04 deo
359.2 g deionized water.

Ca. 720 g of a viscous, clear, slightly yellowish polymer solution were isolated from the reaction vessel. The dry residue amounted to 48.3% by weight. The viscosity of the polymer solution obtained measured 3.75 Pas.

Example 2d

Invention

The following quantities were processed in the same way as in Example 2.
434.9 g (50 mol) Polyglycol E 8000 (polyethylene glycol from Dow Chemical; OHV=13)
37.6 g (202 mol) 2-butyl-1-octanol
39.5 g (162 mmol) m-tetramethyl xylene diisocyanate
0.11 g 1,8-diazabicyclo-[5.4.0]-undec-7-ene (Nitroil)
330.3 g Dehydrol 04 deo
825.8 g deionized water.

In this case, no residual isocyanate could be detected after 2 hours.

Ca. 1650 g of a viscous, clear, slightly yellowish polymer solution were isolated from the reaction vessel. The dry residue amounted to 48.2% by weight. The viscosity of the polymer solution obtained measured 2.25 Pas.

Determination of the Dispersion-Thickening Effect

Quantities of 0.2% of the polymeric active component according to the above Examples (based on and expressed as active substance without Dehydrol 04) were homogenized with a mixture of 31.4% by weight propanediol and 68.6% by weight water. 20 g of the aqueous polyacrylate dispersion Neocryl XK 90 (45% solids content; Neo Resins) were then added and the mixture was homogeneously stirred for ca. 2 mins. using a wooden spatula. After standing for 20 hours, the mixture was again carefully stirred with a wooden spatula. Viscosity was then measured with a Haake RC20-CPS-P Brookfield cone/plate viscosimeter with a C50-1 cone at a shear rate of 300 $s^{-1}$ and then at a shear rate of 4,800 $s^{-1}$. The ICI viscosity of the same sample was then measured with an Epprecht cone/plate viscosimeter (measuring cone C).

The thickening effect of the polyurethane in an aqueous vinyl acetate/ethylene copolymer dispersion (Mowilith LDM 1871, solids content 53%, a Clariant product) was then determined in the same way with the Haake RC20-CPS-P Brookfield cone/plate viscosimeter with a C50-1 cone at a shear rate of 300 $s^{-1}$ and then at a shear rate of 4,800 $s^{-1}$.

The viscosity values obtained are set out in Tables 1 and 2 below. The first column of the Table shows which polymeric active component was used as the HEUR thickener while the second to fifth columns of the Tables—in the interests of clarity—indicate the structural parameters (as indicated in the above Examples) associated with the thickener.

TABLE 1

| | | | | | Dispersion viscosity C/P [mPas] | | | | | |
|---|---|---|---|---|---|---|---|---|---|---|
| | | | | | Neocryl XK90 + diluent | | | Mowilith LDM 1871 + diluent | | |
| Polymer according to Example | PEG:i-$C_{10}$—OH:IPDI ratio [molar] | PEG:i-$C_{10}$—OH:IPDI ratio [equivalent] | x | y | 300 $s^{-1}$ | 4800 $s^{-1}$ | ICI Cone C, 25° C./ 10000 | 300 $s^{-1}$ | 4800 $s^{-1}$ | ICI Cone C 25° C./ 10000 |
| 1 | 1:2:2 | 1:1:2 | 0 | 0 | 665 | 90 | 80 | 250 | 65 | 40 |
| 1a | 1:3:2.8 | 1:1.5:2.8 | 0.5 | 0.4 | 1590 | 135 | 90 | 480 | 85 | 60 |

TABLE 1-continued

| | | | | | Dispersion viscosity C/P [mPas] | | | | | |
| | | | | | Neocryl XK90 + diluent | | | Mowilith LDM 1871 + diluent | | |
| Polymer according to Example | PEG:i-$C_{10}$—OH:IPDI ratio [molar] | PEG:i-$C_{10}$—OH:IPDI ratio [equivalent] | x | y | 300 $s^{-1}$ | 4800 $s^{-1}$ | ICI Cone C, 25° C./ 10000 | 300 $s^{-1}$ | 4800 $s^{-1}$ | ICI Cone C 25° C./ 10000 |
| --- | --- | --- | --- | --- | --- | --- | --- | --- | --- | --- |
| 1b | 1:3.5:3.1 | 1:1.75:3.1 | 0.75 | 0.55 | 1420 | 120 | 90 | 420 | 80 | 70 |
| 1c | 1:4:3.4 | 1:2:3.4 | 1 | 0.7 | 1800 | 135 | 90 | 555 | 90 | 70 |

TABLE 2

| | | | | | Dispersion viscosity C/P [mPas] | | | | | |
| | | | | | Neocryl XK90 + thinner | | | Mowilith LDM 1871 + thinner | | |
| Polymer according to Example | PEG:BuOc-OH:TMXDI ratio [molar] | PEG:BuOc-OH:TMXDI ratio [equivalent] | x | y | 300 $s^{-1}$ | 4800 $s^{-1}$ | ICI Cone C, 25° C./ 10000 | 300 $s^{-1}$ | 4800 $s^{-1}$ | ICI Cone C, 25° C./ 10000 |
| --- | --- | --- | --- | --- | --- | --- | --- | --- | --- | --- |
| 2 | 1:2:2 | 1:1:2 | 0 | 0 | 680 | 145 | 90 | 250 | 100 | 120 |
| 2a | 1:2.4:2.4 | 1:1.2:2.4 | 0.2 | 0.2 | 980 | 170 | 100 | 330 | 110 | 130 |
| 2b | 1:3:2.8 | 1:1.5:2.8 | 0.5 | 0.4 | 1200 | 185 | 110 | 330 | 100 | 150 |
| 2c | 1:3:3 | 1:1.5:3 | 0.5 | 0.5 | 1280 | 185 | 120 | 480 | 120 | 140 |
| 2d | 1:4:3.2 | 1:2:3.2 | 1 | 0.6 | 1350 | 190 | 110 | 450 | 110 | 140 |

Result

It can be seen that, overall, a distinctly better thickening effect is obtained with the polyurethanes according to the invention.

What is claimed is:

1. A thickener based on an aqueous preparation of non-ionic, water-dispersible or water-soluble polyurethane, wherein the polyurethane is obtained, through the formation of an allophanate intermediate, by the reaction of:
   (a) one or more hydrophilic polyols which contain per molecule at least two OH groups and at least two functional groups selected from the group consisting of —O— (ether groups) and —COO— (ester groups), the molecular weight of the hydrophilic compounds being at least 300;
   (b) one or more hydrophobic compounds containing at least one zerewitinoff-active hydrogen atom per molecule, the molecular weight of the hydrophobic compounds ranging from about 100 to about 500 with at least one linear or branched, saturated or unsaturated alkyl chain per molecule, wherein the compound comprises 6 to 24 carbon atoms per molecule and the alkyl chain comprises at least five consecutively linked carbon atoms not linked to a heteroatom; and
   (c) one or more at least difunctional isocyanates,
   wherein components (a), (b) and (c) are reacted with one another in equivalent ratios of $OH_{a)}$:$ZH_{b)}$:$NCO_{c)}$ of 1:(1+x):2(1+y), wherein $OH_{a)}$ is the primary (terminal) OH groups of component (a), $ZH_{b)}$ is the NCO-reactive functional group containing the zerewitinoff-active hydrogen atom of component (b), and $NCO_{c)}$ is the isocyanate group of component (c),
   with the provisos that x is a number of 0.05 to 1.2 and y is a number of (0.2 to 1.05)x, and the ratio of $NCO_{c)}$ equivalents to the sum of $OH_{a)}$ equivalents and $ZH_{b)}$ equivalents is greater than 1 to 1.

2. The thickener according to claim 1, wherein component (a) comprises a polyethylene glycol having a molar weight in the range from 1,000 to 15,000.

3. The thickener according to claim 1, wherein component (b) comprises a C6-24 fatty alcohol.

4. The thickener according to claim 1, wherein component (c) is selected from the group consisting of isophorone diisocyanate and tetramethyl xylene diisocyanate.

5. The thickener of claim 1, wherein x is a number in the range 0.5 to 1.02, and y is a number in the range (0.7 to 1.01) x.

6. The thickener of claim 1, wherein component (b) is selected from the group consisting of alcohols, carboxylic acids, and amines containing 6 to 24 carbon atoms per molecule.

7. A thickener concentrate, comprising:
   (A) water; and
   (B) the thickener according to claim 1.

8. The thickener concentrate according to claim 7, further comprising one or more organic solvents and/or nonionic surfactants in the form of addition compounds of ethylene and/or propylene oxide onto C8-18 alcohols.

9. An emulsion paint comprising the thickener of claim 1.

10. An aqueous dispersion comprising the thickener of claim 1.

11. A cosmetic preparation comprising the aqueous dispersion of claim 10.

12. A cleaning composition comprising the aqueous dispersion of claim 10.

13. A coating composition comprising the aqueous dispersion of claim 10.

14. A cosmetic preparation comprising the thickener of claim 1.

15. A cleaning composition comprising the thickener of claim 1.

16. A coating composition comprising the thickener of claim 1.

* * * * *

UNITED STATES PATENT AND TRADEMARK OFFICE
CERTIFICATE OF CORRECTION

| | | |
|---|---|---|
| PATENT NO. | : 8,334,357 B2 | Page 1 of 1 |
| APPLICATION NO. | : 11/630069 | |
| DATED | : December 18, 2012 | |
| INVENTOR(S) | : Schieferstein et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1000 days.

Signed and Sealed this
Eleventh Day of November, 2014

Michelle K. Lee
*Deputy Director of the United States Patent and Trademark Office*